US006979380B2

(12) United States Patent
Thorson et al.

(10) Patent No.: US 6,979,380 B2
(45) Date of Patent: Dec. 27, 2005

(54) THREE-PIECE DISPOSABLE UNDERGARMENT AND METHOD FOR THE MANUFACTURE THEREOF

(75) Inventors: Russell E. Thorson, Appleton, WI (US); Paul T. Van Gompel, Hortonville, WI (US); Jennifer L. Marvin, Greenville, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 293 days.

(21) Appl. No.: 10/261,805

(22) Filed: Oct. 1, 2002

(65) Prior Publication Data

US 2004/0060648 A1 Apr. 1, 2004

(51) Int. Cl.$^7$ .......................... B32B 31/00; A61F 13/15
(52) U.S. Cl. .................. 156/259; 156/271; 156/265; 156/302; 156/299; 156/300; 156/301; 156/227; 156/226; 156/200; 156/204; 156/164; 156/461; 156/519; 156/552; 156/464
(58) Field of Search ................................ 156/160, 163, 156/164, 201, 204, 226, 227, 265, 299, 300, 156/301, 552, 302, 520, 464, 519, 461, 518, 156/259, 271

(56) References Cited

U.S. PATENT DOCUMENTS

| 3,488,778 A | 1/1970 | Goujon et al. |
| 3,828,367 A | 8/1974 | Bourgeois |
| 4,302,853 A | 12/1981 | Mesek |
| 4,515,595 A | 5/1985 | Kievit et al. |

(Continued)

FOREIGN PATENT DOCUMENTS

EP 0 449 271 A 10/1991

(Continued)

OTHER PUBLICATIONS

International Search Report in corresponding International Application No. PCT/US03/28245, dated Feb. 18, 2004, 7 pages.

(Continued)

*Primary Examiner*—Linda Gray
(74) *Attorney, Agent, or Firm*—Brinks Hofer Gilson & Lione

(57) ABSTRACT

A method of manufacturing a disposable undergarment includes moving a web of body panel material in a longitudinal machine direction and cutting the web of body panel material along the longitudinal machine direction to thereby form a rear body panel web and a front body panel web each having a maximum rise and a minimum rise respectively. The maximum rise of each of the rear and front body panel webs is greater than the minimum rise of a corresponding one of the rear and front body panel webs. The method further includes shifting at least one of the rear and front body panel webs in the longitudinal machine direction and thereby aligning the maximum rises of the rear and front body panel webs. The method further includes separating the rear and front body panels in a lateral cross direction, such that the maximum rises of each of the rear and front body panel webs are spaced apart in the lateral cross direction and form a gap therebetween in a non-overlapping relationship. The method further includes aligning a crotch member with the maximum rises of the front and rear body panels and connecting the crotch member to each of the rear and front body panel webs and thereby bridging the gap therebetween. A disposable undergarment is also provided.

41 Claims, 4 Drawing Sheets

U.S. PATENT DOCUMENTS

| | | |
|---|---|---|
| 4,595,441 A | 6/1986 | Holvoet et al. |
| 4,612,674 A | 9/1986 | Hashimoto |
| 4,652,487 A | 3/1987 | Morman |
| 4,655,760 A | 4/1987 | Morman et al. |
| 4,657,802 A | 4/1987 | Morman |
| 4,663,106 A | 5/1987 | Pomplun et al. |
| 4,663,220 A | 5/1987 | Wisneski et al. |
| 4,707,398 A | 11/1987 | Boggs |
| 4,720,415 A | 1/1988 | Vander Wielen et al. |
| 4,724,184 A | 2/1988 | Killian et al. |
| 4,726,807 A | 2/1988 | Young |
| 4,756,709 A | 7/1988 | Stevens |
| 4,760,764 A | 8/1988 | De Jonckheere et al. |
| 4,781,966 A | 11/1988 | Taylor |
| 4,789,699 A | 12/1988 | Kieffer et al. |
| 4,808,176 A | 2/1989 | Kielpikowski |
| 4,834,738 A | 5/1989 | Kielpikowski |
| 4,863,779 A | 9/1989 | Daponte |
| 4,965,122 A | 10/1990 | Morman |
| 4,981,747 A | 1/1991 | Morman |
| 5,114,781 A | 5/1992 | Morman |
| 5,116,662 A | 5/1992 | Morman |
| 5,151,092 A | 9/1992 | Buell et al. |
| 5,169,706 A | 12/1992 | Collier, IV et al. |
| 5,171,236 A | 12/1992 | Dreier et al. |
| 5,171,239 A | 12/1992 | Igaue et al. |
| 5,226,992 A | 7/1993 | Morman |
| 5,260,126 A | 11/1993 | Collier, IV et al. |
| 5,288,791 A | 2/1994 | Collier, IV et al. |
| 5,330,598 A | 7/1994 | Erdman et al. |
| 5,336,545 A | 8/1994 | Morman |
| 5,366,793 A | 11/1994 | Fitts, Jr. et al. |
| 5,385,775 A | 1/1995 | Wright |
| 5,399,219 A | 3/1995 | Roessler et al. |
| 5,414,470 A | 5/1995 | Hotta et al. |
| 5,496,429 A | 3/1996 | Hasse et al. |
| 5,503,908 A | 4/1996 | Faass |
| 5,569,234 A | 10/1996 | Buell et al. |
| 5,575,783 A | 11/1996 | Clear et al. |
| 5,593,400 A | 1/1997 | O'Leary |
| 5,599,417 A | 2/1997 | Glaug et al. |
| 5,611,790 A | 3/1997 | Osborn, III et al. |
| 5,695,846 A | 12/1997 | Lange et al. |
| 5,716,351 A | 2/1998 | Roe et al. |
| 5,746,730 A | 5/1998 | Suzuki et al. |
| 5,782,819 A | 7/1998 | Tanzer et al. |
| 5,807,368 A | 9/1998 | Helmer |
| 5,817,086 A | 10/1998 | Kling |
| 5,827,259 A | 10/1998 | Laux et al. |
| 5,846,232 A | 12/1998 | Serbiak et al. |
| 5,858,151 A | 1/1999 | Igaue et al. |
| 5,932,497 A | 8/1999 | Morman et al. |
| 5,947,948 A | 9/1999 | Roe et al. |
| 6,015,935 A | 1/2000 | LaVon et al. |
| 6,049,023 A | 4/2000 | Blenke et al. |
| 6,099,516 A | 8/2000 | Pozniak et al. |
| 6,113,717 A | 9/2000 | Vogt et al. |
| 6,120,487 A | 9/2000 | Ashton |
| 6,132,410 A | 10/2000 | Van Gompel et al. |
| 6,149,637 A | 11/2000 | Allen et al. |
| 6,171,432 B1 | 1/2001 | Brisebois et al. |
| 6,187,425 B1 | 2/2001 | Bell et al. |
| 6,217,563 B1 | 4/2001 | Van Gompel et al. |
| 6,217,692 B1 | 4/2001 | Kling |
| 6,258,077 B1 | 7/2001 | Buell et al. |
| 6,264,641 B1 | 7/2001 | Van Gompel et al. |
| 6,264,643 B1 | 7/2001 | Toyoda |
| 6,264,784 B1 | 7/2001 | Menard et al. |
| 6,302,871 B1 | 10/2001 | Nakao et al. |
| 6,306,122 B1 | 10/2001 | Narawa et al. |
| 6,323,389 B1 | 11/2001 | Thomas et al. |
| 6,325,787 B1 | 12/2001 | Roe et al. |
| 6,336,922 B1 | 1/2002 | VanGompel et al. |
| 6,352,528 B1 | 3/2002 | Weber et al. |
| 6,359,192 B1 | 3/2002 | Schmidt et al. |
| 6,364,863 B1 | 4/2002 | Yamamoto et al. |
| 6,367,089 B2 | 4/2002 | Van Gompel et al. |
| 6,375,646 B1 | 4/2002 | Widlund et al. |
| 6,387,471 B1 | 5/2002 | Taylor et al. |
| 6,827,804 B2 * | 12/2004 | Otsubo et al. ............... 156/161 |
| 2001/0025164 A1 | 9/2001 | Krautkramer et al. |
| 2001/0025165 A1 | 9/2001 | Shimoe |
| 2001/0047159 A1 | 11/2001 | Mizutani |
| 2002/0002021 A1 | 1/2002 | May et al. |
| 2002/0009940 A1 | 1/2002 | May et al. |
| 2002/0010450 A1 | 1/2002 | Suzuki et al. |
| 2002/0104608 A1 | 8/2002 | Welch et al. |
| 2003/0121614 A1 * | 7/2003 | Tabor et al. ................. 156/552 |
| 2005/0010188 A1 | 1/2005 | Glaug et al. |

FOREIGN PATENT DOCUMENTS

| | | |
|---|---|---|
| EP | 0 753 292 A2 | 1/1997 |
| EP | 0 794 751 B1 | 6/1999 |
| EP | 1 108 372 A1 | 6/2001 |
| EP | 0 907 510 B1 | 3/2002 |
| EP | 1 240 881 A2 | 9/2002 |
| EP | 1 249 214 A | 10/2002 |
| EP | 1 366 735 A1 | 12/2003 |
| EP | 1 428 487 A1 | 6/2004 |
| FR | 2644694 | 9/1990 |
| JP | 03176053 A | 7/1981 |
| JP | 2001-29389 * | 2/2001 |
| WO | WO 93/17648 | 9/1993 |
| WO | WO 98/29251 A | 7/1998 |
| WO | WO 99/56688 A1 | 11/1999 |
| WO | WO 00/39201 A | 6/2000 |
| WO | WO 01/87588 A2 | 11/2000 |
| WO | WO 01/87589 A2 | 11/2001 |
| WO | WO 01/88245 A2 | 11/2001 |
| WO | WO 02/24131 A1 | 3/2002 |

OTHER PUBLICATIONS

Patent Application entitled, "Body Conforming Absorbent Garment and Methods for the Use and Manufacture Thereof", U.S. Appl. No. 10/274,503, filed on Oct. 18, 2002.

Patent Application entitled, "Disposable Undergarment with a Stretchable Absorbent Insert and Method for the Use and Thereof", U.S. Appl. No. 10/325,500, filed on Dec. 19, 2002.

International Search Report in related International Application No. PCT/US03/28637, dated Jan. 22, 2004, 9 pages.

International Search Report in related International Application No. PCT/US03/39405, dated Apr. 16, 2004, 6 pages.

International Search Report in International Application No. PCT/US2004/008429, dated Aug. 17, 2004, 7 pages.

* cited by examiner

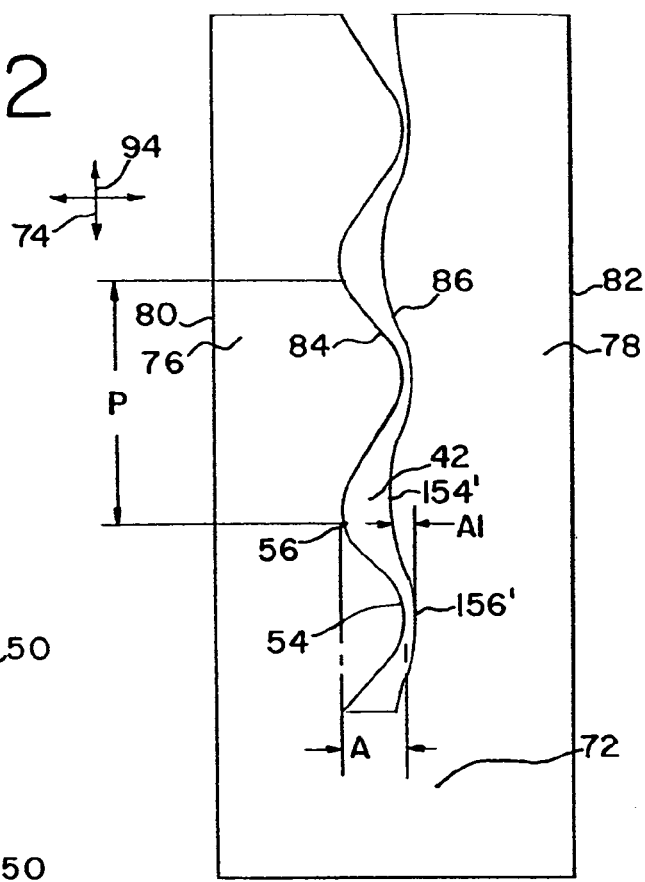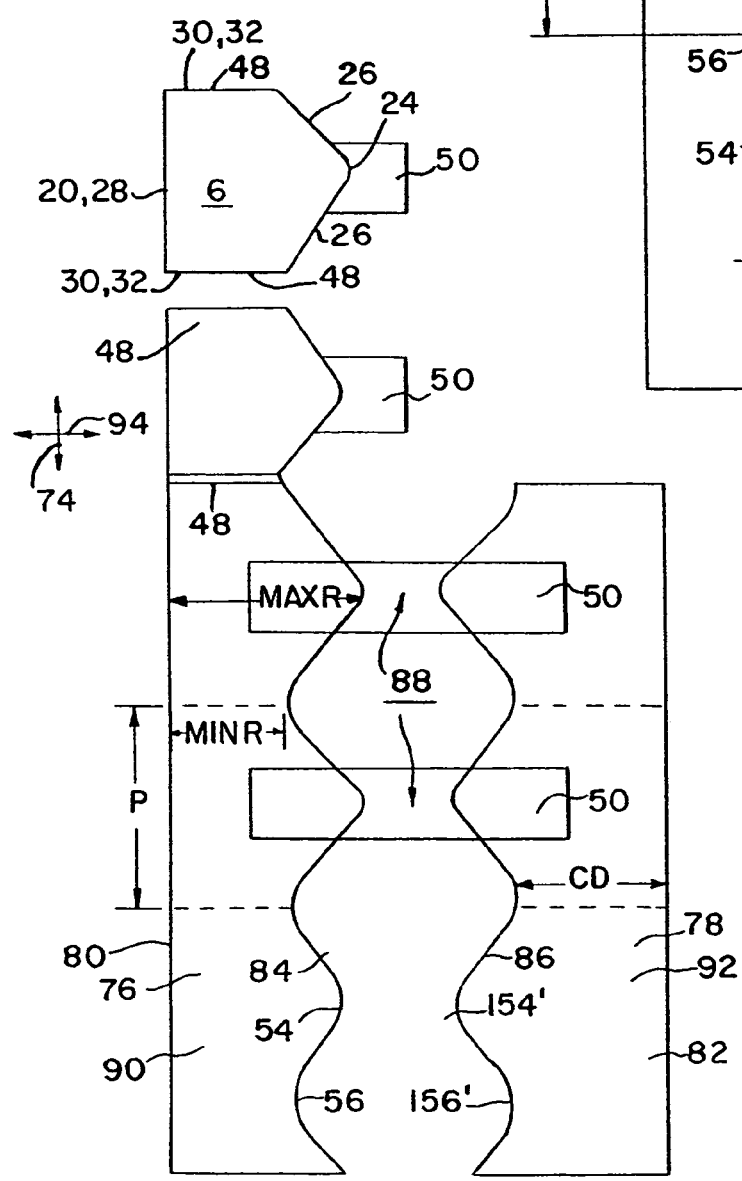

THREE-PIECE DISPOSABLE UNDERGARMENT AND METHOD FOR THE MANUFACTURE THEREOF

BACKGROUND

The present invention relates generally to disposable undergarments, and in particular, a three-piece undergarment and the method for the manufacture thereof from a nested front and rear body panel web.

Disposable undergarments can be configured in many different forms For example, disposable absorbent garments can be configured as a pant-type, pull-on garment, or as a diaper-type product that is drawn up between the legs and fastened about the waist with various fastening systems. Often, absorbent garments include an outer cover, which forms at least a part of a body panel that is secured around the waist of the user. In addition, the outer cover typically extends along a crotch region of the garment.

Often, the outer cover is made from a single piece of material, with leg openings cut therein, for example by die cutting. The material from the leg cut out, which can account for as much as 20–30% of the total area of the outer cover, typically is waste material, which must be disposed of or recycled.

In response to this problem of waste, some garments are configured with front, rear and crotch sections formed from a single web that is divided into two nested halves, as disclosed for example in U.S. Pat. No. 5,858,151 and Japanese Patent Application 03-176053 A. However, the webs of the U.S. Pat. No. 5,858,151 have overlapping crotch portions that are directly secured one to the other. Accordingly, the overall rise of the garment is not readily varied to accommodate different size users, and the range of sizes is limited by the extent of the overlapping regions.

Conversely, the diaper body of Japanese Patent Application 03-176053 A is positioned over the cut-out portions of a front and back waistband, such that the exposed portion of the waist bands defining in part the leg holes are linear. Instead, the shape of the leg hole is determined by the cut shape of the diaper body, which produces excess material that must be disposed of or recycled.

Moreover, the size of the leg openings formed by a die cutter in a conventional one-piece outer cover is typically fixed. As such, it can be expensive and time consuming, and reduces the overall flexibility of the manufacturing line, to switch dies and alter the process to manufacture different size garments.

Therefore the need remains for improved methods and assemblies for manufacturing undergarments to reduce the waste of materials while providing flexibility in manufacturing different size garments.

SUMMARY

Briefly stated, in one preferred embodiment described below, a method of manufacturing an undergarment includes moving a web of body panel material in a longitudinal machine direction and cutting the web of body panel material along the longitudinal machine direction to thereby form a rear body panel web and a front body panel web each having a maximum rise and a minimum rise respectively. The maximum rise of each of the rear and front body panel webs is greater than the minimum rise of a corresponding one of the rear and front body panel webs. The method further includes shifting at least one of the rear and front body panel webs in the longitudinal machine direction and thereby aligning the maximum rises of the rear and front body panel webs. In addition, the method includes separating the rear and front body panels in a lateral cross direction, such that the maximum rises of each of the rear and front body panel webs are spaced apart in the lateral cross direction and form a gap therebetween in a non-overlapping relationship. The method further includes aligning a crotch member with the maximum rises of the rear and front body panel webs and connecting the crotch member to the front and rear body panels and thereby bridging the gap therebetween.

In a preferred embodiment, the cutting of the web of body panel material along the longitudinal machine direction includes forming a substantially sinusoidal pattern defining the maximum and minimum rises of each of the rear and front body panel webs.

In one preferred embodiment, the front and rear body panel webs are cut along the lateral cross direction proximate the minimum rise of each of the front and rear body panel webs. Also in a preferred embodiment, the crotch member is folded.

In another aspect, a die is used to cut the web of body panel material. In one preferred embodiment, the method includes forming a cut edge along each of the front and rear body panel webs, wherein the cut edges of the front and rear body panel webs have a first and second shape respectively. In one preferred embodiment, the first shape is different than the second shape.

In another aspect, the wave pattern defining the cut edges of the front and rear body panel webs is not symmetrical relative to a centerline extending in the longitudinal machine direction. In particular, the curve defining the cut edge on one side of the centerline has a different shape than the curve defining the cut edge on the other side of the centerline. In one example, the curves, if continuous on both sides of the centerline, would have a different wavelength.

In another aspect, one preferred embodiment further includes elongating the web of body panel material in the longitudinal machine direction before cutting the web of body panel web. In this way, the pitch of the garment can be easily changed simply by varying the amount of elongation introduced into the web before the web is cut.

In yet another aspect, one preferred embodiment of the method further includes varying the gap formed between the maximum rises of each of the rear and front body panel webs. In this way, the overall rise of the garment can be easily changed simply by varying the gap.

In various preferred embodiments, elastic elements are positioned along one or more of the outer lateral edges of the inner cut edge of one or more of the webs.

In yet another aspect, a disposable undergarment includes a front and rear body panel each having a pair of opposite side edges, a terminal edge and a cut edge spaced from said terminal edge and defining a substantially curvilinear and sinusoidal wave pattern. The wave patterns further define maximum rises and minimum rises of the front and rear body panels along a first direction. Preferably, the maximum rise of each body panel is greater than the minimum rise of the same body panel such that the respective cut edge further defines an amplitude of the respective wave pattern. The opposite side edges are spaced along a second direction, which is substantially perpendicular to the first direction, with the opposite side edges defining a pitch of the respective wave patterns. In one preferred embodiment, the amplitudes of the front and rear body panels are preferably different, while the pitches of the front and rear body panels are preferably the same. A crotch member is preferably connected to the front and rear body panels.

The foregoing paragraphs have been provided by way of general introduction, and are not intended to limit the scope of the following claims. The presently preferred embodiments, together with further advantages, will be best understood by reference to the following detailed description taken in conjunction with the accompanying drawings.

BRIEF DESCRIPTION OF THE DRAWINGS

FIG. 2 is a plan view of a web of body panel material being cut along a longitudinal machine direction.

FIG. 3 is a plan view of a front and rear body panel web with a plurality of absorbent inserts being applied thereto.

DETAILED DESCRIPTION OF THE PRESENTLY PREFERRED EMBODIMENTS

Figure 1:
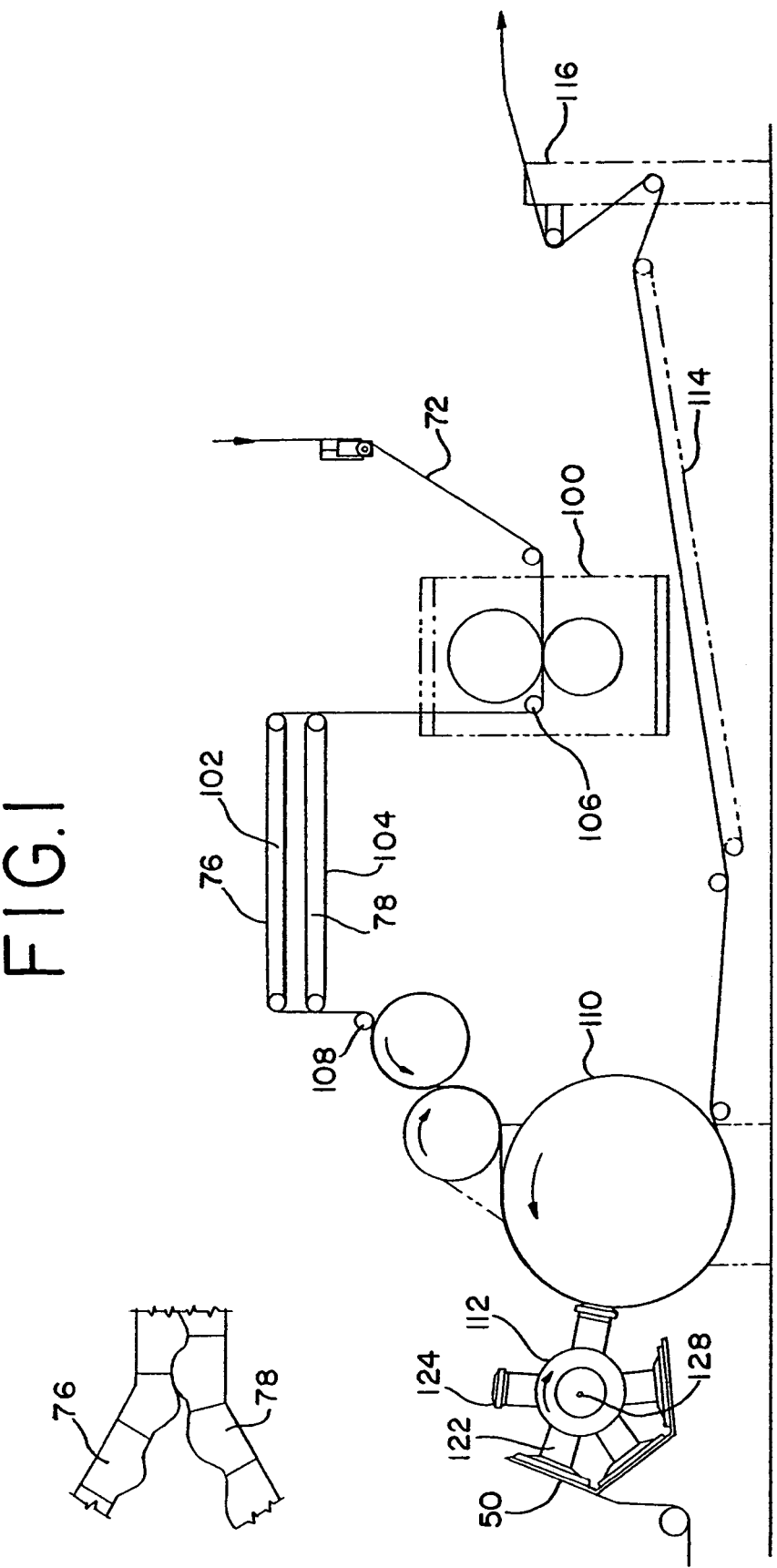
FIG. 1 is a schematic illustration of a system for manufacturing an absorbent garment.

It should be understood that the term "longitudinal," as used herein, means of or relating to length or the lengthwise direction. The term "laterally," as used herein means situated on, directed toward or running from side to side.

The term "bodyside" should not be interpreted to mean in contact with the body of the user, but rather simply means the side that would face toward the body of the user, regardless of whether an undergarment is actually being worn by the user and regardless of whether there are or may be intervening layers between the component and the body of the user. Likewise, the term "garment side" should not be interpreted to mean in contact with the garments of the user, but rather simply means the side that faces away from the body of the user, and therefore toward any outer garments that may be worn by the user, regardless of whether the undergarment is actually being worn by a user, regardless of whether any such outer garments are actually worn and regardless of whether there may be intervening layers between the component and any outer garment.

The term "machine direction" means the direction of flow as the various members and webs progress along the fabrication line and process. It should be understood that various separate members or webs can each be traveling in a machine direction, but with the various machine directions not necessarily being parallel or oriented in the same direction. For example, a first component such as a web may be traveling a first machine direction, which is substantially perpendicular to the travel of another component, such as an absorbent insert, in a second machine direction.

The term "cross direction" means the direction substantially perpendicular to the machine direction.

The term "downstream" means that one item is positioned more closely to the output or finished product end of the machine and/or process relative to another item. Conversely, the term "upstream" means that an item is positioned more closely to the input end of the machine or process relative to another item. For example, the output end is downstream of the input end, and vice versa, the input end is upstream of the output end.

The phrases "removeably attached," "removeably attaching," "removeably connected," "removeably engaged," "releasably attached," "releasably connected," or "releasably engaged," and variations thereof, refers to two or more elements being connected or connectable such that the elements tend to remain connected absent a separation force applied to one, both or all of the elements, and where the elements are capable of being separated upon the application of a separation force. The required separation force is typically beyond that encountered while wearing the absorbent garment.

The phrases "fixedly secured," "fixedly engaged," "fixedly attached," "fixedly connected," and variations thereof, refers to two or more elements being connected or connectable such that they are not disconnected or otherwise separated, and are not intended to be separated or disconnected, during the normal operation and use of the absorbent garment.

The term "web" refers to a continuous stream of material, whether made from one or more layers or substrates, and regardless of whether it may have non-continuous, discrete items disposed thereon.

The terms "connecting," "coupled," "attached," and "secured," and variations thereof, broadly covers two or more items being directly connected one to the other, or by way of one or more intervening members or components.

Figure 4:
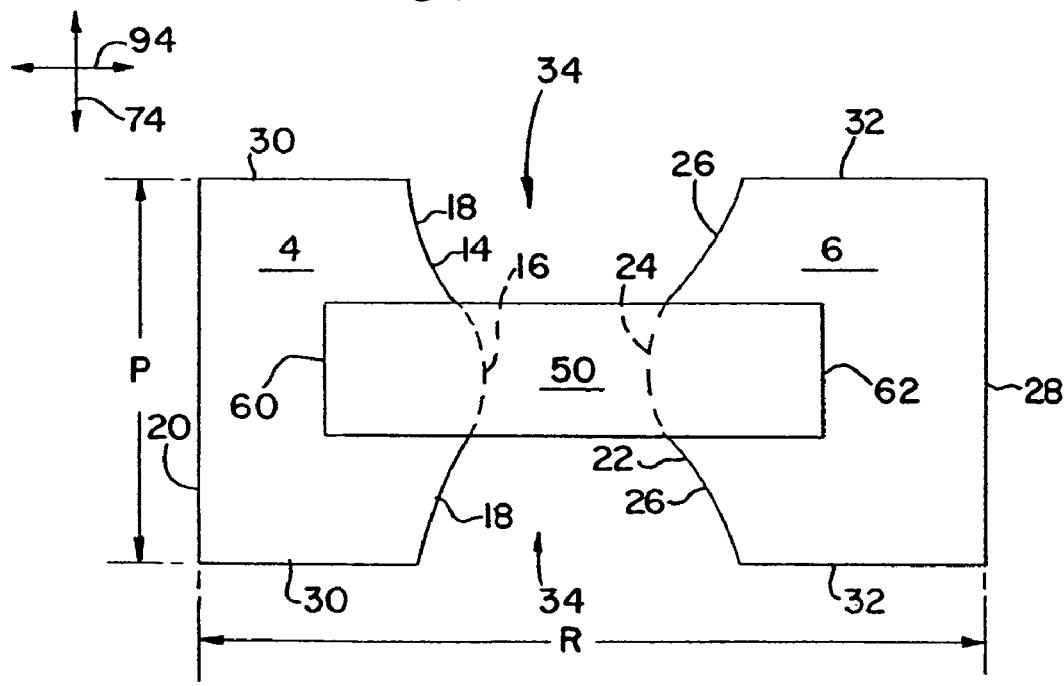
FIG. 4 is a plan view of one embodiment of an absorbent garment in an unfolded configuration.
Figure 5:
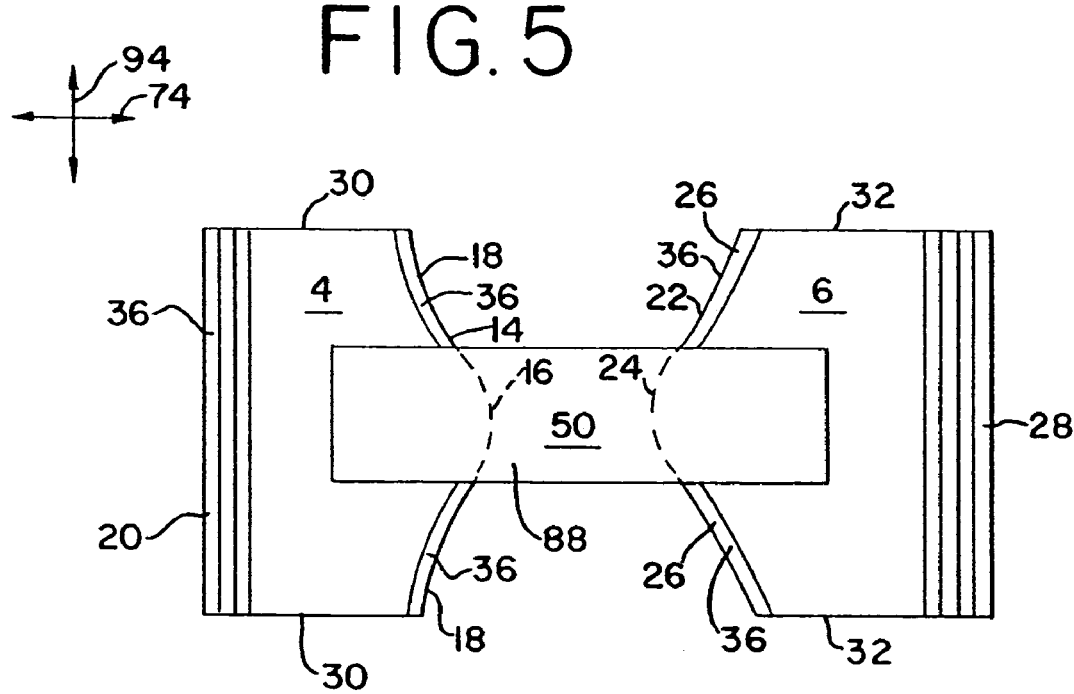
FIG. 5 is a plan view of another embodiment of an absorbent garment in an unfolded configuration.

Referring to FIGS. 4 and 5, an undergarment 2 includes a first, front body panel 4 and a second, rear body panel 6. The term "body panel" refers to the portion(s) of the undergarment, whether made of one or more layers or substrates or of one or more pieces or components, that is/are fitted circumferentially around at least the waist region of the user, including for example the user's lower back, buttock, hips and abdomen. The first and second body panels each have an inner, bodyside surface 10 and an outer, garment side surface 12. The first, front body panel 4 has a first edge 14 forming a crotch portion 16 and leg opening portion 18 and a second terminal edge 20 which is preferably linear but can assume other shapes. Likewise, the second, rear body panel 6 has a first edge 22 forming a crotch portion 24 and a leg opening portion 26 and a second terminal edge 28, which is preferably linear but can assume other shapes. Each of the first and second body panels has an outboard side edge 30, 32 formed along the outer periphery of the opposite side portions of the first and second body panel. It should be understood that the outboard side edges of the front and rear body panels can have different lengths relative to each other.

Referring to FIG. 4, one or more, and preferably a plurality, meaning two or more, elastic elements 36 are secured to each of the first and second body panels. In one preferred embodiment, a plurality of elastic elements are spaced across substantially the entire waist portion of the front and rear body panel 4, 6, although they may be spaced across a lesser length. For example, elastic elements can extend along the upper waist portion and along the lower terminal edge defining in part a leg opening 34.

In one embodiment, the front body panel has a "non-elasticized" area wherein there are no elastic elements, or other elastic or elastomeric backing members, incorporated therein or making up any portion of the thickness or cross-section of the body panel at that area. It should be understood, that in an alternative embodiment, one or more separate waist bands, with or without elastic elements, can be secured to one or both of the rear and front body panels, preferably along the upper terminal edges 20, 28 thereof. Likewise, one or more separate leg bands can be secured to one or both of the rear and front body panels along the leg open portions 18, 26 adjacent the leg openings 34. Alternatively, one or both of the body panels can be formed without any elastic elements as shown in FIG. 5.

The various waist and leg elastic elements can be formed from rubber or other elastomeric materials. One suitable material is a LYCRA® elastic material. For example, the various elastic elements can be formed of LYCRA® XA Spandex 540, 740 or 940 decitex T-127 or T-128 elastics available from E.I. duPont De Nemours and Company, having an office in Wilmington, Del.

Referring to FIGS. 4 and 5, each body panel 4, 6 is preferably formed as a composite, or laminate material, otherwise referred to as substrates or laminates, with the plurality of elastic strands sandwiched therebetween. Preferably two or more layers are bonded with various adhesives, such as hot melt, or by other techniques, including for example and without limitation ultrasonic bonding and heat pressure sealing. In one embodiment, the two layers are made of a non-woven material such as a spunbond material, a bonded carded material or other known materials. It should be understood that the body panels can be made of a single layer or substrate of non-woven material, or can be comprised of more than two layers or substrates. Of course, it should be understood that other knitted or woven fabrics, non-woven fabrics, elastomeric materials, polymer films, laminates and the like can be used to form one or more of the body panel layers. The term "non-woven" web or material, as used herein, means a web having a structure of individual fibers or filaments that are interlaid, but not in an identifiable manner and without the aid of textile weaving or knitting, as in a knitted or woven fabric.

In one embodiment, the body panel material can be secured to the elastic elements, such as strands or ribbons, which have been elongated and retracted, such that the material is gathered when the elastic elements are relaxed. Alternatively, the material can be gathered and laminated to non-elongated elastic elements. In one preferred embodiment, the body panel includes a gathered elastic laminate made from nonwoven base sheets bonded with elongated elastic elements sandwiched therebetween.

In various preferred embodiments, the body panel material may be substantially permeable to air or substantially impermeable to air. The body panel material also may be substantially liquid-permeable or substantially liquid-impermeable. In particular arrangements, the body panel material may be substantially nonelastomeric. In other aspects, the body panels can include an elastomeric material that is elastomerically stretchable at least along the lateral article width. Examples of such elastomeric composite materials can include a vertical filament laminate (VFL), neck-bonded-laminate (NBL), a stretch-bonded-laminate (SBL), a necked-stretch bonded laminate (NSBL) or a necked-thermal laminate, or the like, as well as combinations thereof. Exemplary NBL, SBL, and NSBL materials are described in U.S. Pat. Nos. 5,226,992, 4,981,747, 4,965,122, 5,336,545, 5,385,775, 5,414,470,4,720,415, 4,789,699, 4,781,966, 4,657,802, 4,652,487, 4,655,760, 5,116,662 and 5,114,781, all of which are hereby incorporated herein by reference. Exemplary VFL materials are described in U.S. Provisional Patent Application Ser. No. 60/204,307, filed May 15, 2000 and entitled "Method and Apparatus for Producing Laminated Articles," and PCT application WO 01/88245 A2, both assigned to Kimberly-Clark Worldwide, Inc., the Assignee of the present application, with the entire disclosures of both being hereby incorporated herein by reference. Such laminates can provide an improved combination of cloth-like feel and elastomeric stretchability. The body panels can be composed of materials that are elastic or elastomeric and exhibit biaxial stretch characteristics or MD/CD stretch characteristics, or that are extensible composites. Additional waist and leg elastic elements can be added to, but are not necessarily required by, the body panels.

In preferred embodiment, the entirety of the body panels are elasticized, such that the entire body panel conforms to the body of the user without any spacing between the body panel and the user's body, and without the attendant bulkiness of a non-elasticized material.

Preferably, the body panels are breathable, cloth-like, multi-directional nonwoven laminates with stretch and/or extensible properties. In one preferred embodiment, the non-woven layers are pre-necked, preferably between about 10% and about 80%, in the longitudinal direction, which provides extensibility in the longitudinal direction with minimum force.

The terms "extensible," "extensibility," and variations thereof as used herein means capable of being extended, and providing a selected elongation, for example between about 5% and about 70%, when subjected to an applied tensile force. The body panel also is preferably capable of providing a selected, sustained deformation when subjected to an applied tensile force and then allowed to relax for a selected time period beginning immediately after removal of the tensile force. Preferably the sustained deformation is a substantially permanent deformation. The selected elongation and sustained deformation preferably occur at least along the longitudinal direction of the garment, although it should be understood that it also could occur along the lateral direction, or both. Various extensible materials, and other acceptable materials that can be used for the body panels are described for example in U.S. Pat. No. 6,217,563, issued Apr. 17, 2001 to Kimberly-Clark Worldwide, Inc., the same Assignee as the present application, the entire disclosure of which is hereby incorporated herein by reference.

The extensibility of the preferred non-woven material provides an increase in surface area without the retractive force of elastomeric materials. In one preferred embodiment, body panel is extensible in at least the cross-direction, or longitudinal direction, with the material providing an elongation of at least about 1 cm when subjected to a tensile force of 11.8 grams per cm. In addition, the body panel preferably provides a substantially permanent deformation of at least about 20% when it is subjected to a tensile force of 19.70 grams per cm and is then allowed to relax under a zero applied stress for a period of 1 minute. Of course, it should be understood that the body panel can also be made extensible in the lateral direction.

In one preferred embodiment, the front and rear body panels 4, 6 are made of non-woven laminates of two layers of longitudinally extensible 0.60 osy polypropylene spunbond material with elongated strands of Lycra® elastic sandwiched between the spunbond layers and thereafter adhesively bonded. In particular, the body panel material is necked in the cross direction. As used herein, the term "necked," and variations thereof, refers to any material that has been constricted in at least one dimension by applying a tensioning force in a direction that is perpendicular to the desired direction of neck-down. Processes that may be used to constrict a material in such a manner include, for example and without limitation, drawing processes. The elastics are then elongated in the machine direction and secured to the body panel material The elastics are then allowed to retract so as to gather the necked spunbond material in the lateral (machine) direction thereby creating an elastically gathered non-woven body panel with longitudinal extensibility. The term "gather," and variations thereof, as used herein means puckered, or contracted into folds or wrinkles, which should be understood as including micro-pleats. In this way, the body panel can be elongated in both the longitudinal and lateral direction to conform to the body of the user when the garment is applied thereto. In particular, as the user pulls the garment up over their hips, the non-woven laminate body panels stretch in the lateral direction while the leg regions of the front and rear body panels conform to the crotch and body lines of the user. At the same time, the body panel material extends in the longitudinal direction to conform to the buttocks and stomach of the user. The extensibility of the body panels follows the natural curvature of user's body to provide conformance thereto. As the body panel extends in the longitudinal direction, the spacing between the laterally extending elastic elements 36, incorporated in one preferred embodiment, will increase.

The body panel 4, 6 non-woven material is preferably substantially hydrophobic, which may optionally be treated with a surfactant or otherwise processed to impart a desired level of wettability and hydrophilicity. In one particular embodiment of the invention, the body panel is a nonwoven, wireweave spunbond polypropylene fabric composed of about 1.6 denier fibers formed into a web having a basis weight of about 0.6 osy. One suitable non-woven material is the Corinth 0.60 osy, 1.6 dpf wireweave, nonwettable Metallocene (EXXON ACHIEVE 2854 PP) spunbond material manufactured by Kimberly-Clark Corporation, the assignee of the present application.

Referring to FIGS. 4 and 5, a crotch member 50 connecting the front and rear body panels 4, 6 can be folded such that the side edges 30, 32 of the front and rear body panels 4, 6 are aligned wherein they can be fixedly secured at a seam. The seam can be formed by bonding, sewing or otherwise attaching the side edges. Alternatively, the product can remain "open," wherein the body panels are releasably secured with one or more fastening members as explained below.

In one preferred embodiment the garment includes a combination of side edges that are secured to form a seam and fastening members that allow the fit of the undergarment to be adjusted. For example, fastening members are preferably attached to the front body panel and extend inboard relative to the outboard side edge 30 of the front body panel 4 from an attachment location, which is preferably spaced inboard from the side edge. A landing member can be formed on or secured to the body panel to receive a refastenable portion of the fastening member. One or more lines of weakness can be provided along the front or rear body panel such that one or both of the body panels are breakable. The lines of weakness can comprise a perforation or other series of cuts, a thinning, breakage or separation of material, or a strip of a different kind of material bridging portions of the body panel that is more easily torn or broken than the other material thereof, which allow a user or the manufacturer to separate portions of the body panel. For example, the undergarment can be broken along the lines of weakness after the garment is applied to a user, or beforehand. Preferably, the fastening members are secured to the garment-side surface of the body panel.

It should be understood that, in other embodiments, the fastening members can be secured to the rear body panel and engage the front body panel or, conversely, can be secured to the front body panel and engage the rear body panel, preferably along at least a portion that is not elasticized. Preferably, the fastening members are fixedly secured to the outer, garment-side surface of the front and/or rear body panels, and releasably engage the outer, garment-side surface of the front and/or rear body panels, although it should be understood that the fastening members could be fixedly secured to an inner body-side surface of front and/or rear body panels and releasably engage an inner, body-side surface of the front and/or rear body panels.

When incorporated into a disposable absorbent undergarment, the fastening members preferably include a refastenable portion, such as an array of hook members, adhesives, such as pressure sensitive adhesives, buttons, zippers, snaps and other releasable and reattachable fastening devices. In various preferred embodiments, the fastening member includes one, two or more than two tab members. In one embodiment, the fastening members comprise a carrier member, which is preferably fixedly secured to the side portions of the front body panel with adhesive bonds, sonic bonds, thermal bonds, pinning, stitching or other known types of attachment. In alternative embodiments, the fastening members can be fixedly secured to the rear body panel or to one or both of the front and rear body panels, for example, at the seam, as explained above.

Referring to FIGS. 4 and 5, in a preferred embodiment the undergarment is disposable and is also configured as an absorbent undergarment. In the absorbent garment, the crotch member includes an absorbent insert 50 having first and second opposed terminal end edges 60, 62. In one preferred embodiment, the absorbent insert preferably includes a substantially liquid permeable topsheet, or liner, and a substantially liquid impermeable backsheet, or outer cover. A retention portion is disposed or sandwiched between the topsheet and the backsheet, which are connected. The topsheet, backsheet and other components of the absorbent insert 50 can be joined for example with adhesive bonds, sonic bonds, thermal bonds, pinning, stitching or any other attachment techniques known in the art, as well as combinations thereof. For example, a uniform continuous layer of adhesive, a patterned layer of adhesive, a sprayed pattern of adhesive or any array of lines, swirls or spots of construction bonds may be used to join the topsheet and backsheet, or any of the other components described herein. It should be understood that the term "absorbent insert" refers to any material or assembly capable of absorbing liquids or bodily exudates, and may be comprised of a single material or component, for example a retention portion, or can be formed as a composite of several components. It should also be understood that the term "crotch member" refers to any member made of any material, including for example and without limitation those described herein with respect to the body panels and absorbent inserts, and is not limited to absorbent inserts and/or materials. For example, the crotch member may be made of one or more layers of a non-woven material.

In one preferred embodiment, additional layers, including for example, a surge layer, are also preferably incorporated into the absorbent insert. Preferably, the surge layer does not run the entire length of the absorbent insert and is shorter than the retention portion. The topsheet can be indirectly joined to the backsheet by affixing the topsheet to intermediate layers, such as the surge layer or retention portion, which in turn is affixed to the backsheet. The absorbent insert also may include barrier cuffs, or leakage control shields, formed along the opposite longitudinally extending edges of the absorbent composite.

The backsheet is preferably liquid impermeable, but may be liquid permeable, e.g., when an additional barrier layer is used with the retention portion. For example, in one embodiment, the backsheet can be made from a thin plastic film, or other flexible, substantially liquid-impermeable material. As used herein, the term "flexible" means a material that is compliant and which will readily conform to the general shape and contour of the body of the user. The backsheet prevents various bodily fluids and exudates from wetting or otherwise contaminating various bedding or outer garments worn by the user over the absorbent garment. In particular, the backsheet can include a film, such as a polyethylene film, having a thickness of from about 0.012 mm to about 0.051 mm.

In various constructions, the topsheet can comprise various woven or nonwoven materials. For example, the topsheet can be composed of a meltblown or spunbonded web of desired fibers, and may also be a bonded-carded web. For example, the topsheet can be made of a substantially hydrophobic material, and the hydrophobic material may optionally be treated with a surfactant or otherwise processed to import a desired level of wettability and hydrophilicity. In one particular embodiment of the invention, the topsheet is a nonwoven, spunbond polypropylene fabric composed of about 2.8–3.2 denier fibers formed into a web having a basis weight of about 22 gsm and density of about 0.06 gm/cc. The fabric can be surface treated with an operative amount of surfactant, such as about 0.28% Triton X-102 surfactant. The surfactant can be applied by any conventional means, such as spraying, printing, brush coating or the like.

In various constructions, the backsheet can comprise a woven or nonwoven fibrous web layer, which is treated or constructed, partially or wholly, to impart the desired levels of liquid impermeability to selected regions that are adjacent to or proximate the absorbent retention portion. For example, the backsheet may include a gas-permeable, nonwoven fabric layer laminated to a polymer film layer which may or may not be gas-permeable. Other examples of fibrous, cloth-like backsheet materials can comprise a stretch thinned or stretch thermal laminate material composed of a 0.6 mil (0.015 mm) thick polypropylene cast film and a 0.7 ounce per square yard (23.8 gsm) polypropylene spunbond material (2 denier fibers). A material of this type has been employed to form the outercover of a HUGGIES® Ultratrim Disposable Diaper, which has been commercially available from Kimberly-Clark Corporation. The backsheet can provide the outercover of the article, particularly in the crotch region. Optionally, however, the article may include a separate outercover component member, as disclosed herein, which is additional to the backsheet. The outercover can be joined, for example, to one or more of the absorbent composite and/or body panels as explained above.

The backsheet may include a micro-porous, "breathable" material which permits gases, such as water vapor, to escape from the absorbent garment while substantially preventing liquid exudates from passing through the backsheet. For example, the breathable backsheet may be composed of a microporous polymer film or a nonwoven fabric which has been coated or otherwise modified to impart a desired level of liquid impermeability. For example, a suitable microporous film can be a PMP-1 material, which is available from Mitsui Toatsu Chemicals, Inc., a company having offices in Tokyo, Japan; or an XKO-8044 polyolefin film available from 3M Company of Minneapolis, Minn. The backsheet may also be embossed or otherwise provided with a pattern or matte finish to exhibit a more aesthetically pleasing appearance.

In various configurations of the invention, where a component, such as the backsheet is configured to be permeable to gas while having a resistance and limited permeability to aqueous liquid, the liquid resistant component can have a construction which is capable of supporting a selected hydrohead of water substantially without leakage therethrough. A suitable technique for determining the resistance of a material to liquid penetration is Federal Test Method Standard FTMS 191 Method 5514, 1978, or an equivalent thereof.

In one preferred embodiment, the backsheet is sufficiently impermeable to liquid and semi-liquid materials to substantially prevent the undesired leakage of waste materials, defined as exudates, including for example urine and feces. For example, the backsheet member can desirably support a hydrohead of at least about 45 centimeters (cm) substantially without leakage. The backsheet member can alternatively support a hydrohead of at least about 55 cm, and optionally, can support a hydrohead of at least about 60 cm, or more, to provide improved benefits.

The backsheet and/or outercover also can be extensible. In one preferred embodiment, the backsheet and/or outercover is capable of providing an elongation of at least about 1 cm when subjected to a tensile force of 11.8 g/cm, and further provides a substantially permanent deformation of at least about 20% when subjected to a tensile force of 19.70 g/cm and is then allowed to relax under a zero applied stress for a period of 1 minute.

For example, the extensible member can be composed of a necked fiber, a creped fiber, a micro-pleated fiber, polymer films or the like, as well as combinations thereof. The fabrics may be woven or nonwoven materials, such as spunbond fabrics. One example of a suitable extensible material is a 60% necked, polypropylene spunbond having a basis weight of about 1.2 osy.

The backsheet and/or outercover also can be expandable, for example when it has one or more folds, e.g., one or more z-folds (not shown), or can be both extensible and expandable. The term expandable as used herein means to enlarge or to increase the extent or area, lateral and/or longitudinal, thereof, e.g., by unfolding one or more folds.

The retention portion is preferably made of an absorbent material, which can be any material that tends to swell or expand as it absorbs exudates, including various liquids and/or fluids excreted or exuded by the user. For example, the absorbent material can be made of airformed, airlaid and/or wetlaid composites of fibers and high absorbency materials, referred to as superabsorbents. Superabsorbents typically are made of polyacrylic acids, such as FAVOR 880 available from Stockhausen, Inc. of Greensboro, N.C. The fibers can be fluff pulp materials, such as Alliance CR-1654, or any combination of crosslinked pulps, hardwood, softwood, and synthetic fibers. Airlaid and wetlaid structures typically include binding agents, which are used to stabilize the structure. In addition, various foams, absorbent films, and superabsorbent fabrics can be used as an absorbent material. Various acceptable absorbent materials are disclosed in U.S. Pat. No. 5,147,343 for Absorbent Products Containing Hydrogels With Ability To Swell Against Pressure, U.S. Pat. No. 5,601,542 for Absorbent Composite, and 5,651,862 for Wet Formed Absorbent Composite, all of which are hereby incorporated herein by reference. Furthermore, the proportion of high-absorbency particles can range from about 0 to about 100%, and the proportion of fibrous material from about 0 to about 100%. Additionally, high absorbency fibers can be used such as Oasis type 121 and type 122 superabsorbent fibers available from Technical Absorbent Ltd., Grimsby, Lincolnshire, United Kingdom.

The retention portion preferably can be made of a single or dual layer of absorbent material. The retention portion preferably has an hour-glass shape with enlarged end regions. Alternatively, the retention portion can include a folded or multi-layered configuration. The retention portion preferably has a length substantially equal to, or slightly shorter than, the length of the absorbent insert. The retention portion can include one or more barrier layers attached to the absorbent material. In one embodiment, an upper tissue substrate is disposed adjacent the retention portion. Alternatively, a lower tissue substrate can be disposed adjacent an opposite side of the retention portion, or the tissue can completely envelope the retention position.

Referring to FIGS. 4 and 5, the opposite garment side of the end regions of the crotch member 50, and in particular, the outer, garment side surface of the backsheet, are secured to the bodyside surface of the opposed crotch portions 16, 24 of the first and second body panels 4, 6. It should be understood that in an alternative preferred embodiment, the crotch member, for example the body side thereof, can be secured to the garment side surface of the first and second body panels. It should be understood that the crotch member 50 can be secured using any of the methods of attachment described above, including for example various adhesives, stitching or other bonding methods. The crotch member can be secured to the body panels with any configuration of attachment lines, swirls, patterns, spots, etc., or can be a full and continuous attachment therebetween.

The entire portion of the crotch member 50 overlapping the body panels 4, 6 can be attached thereto, or the crotch member can be minimally attached to the body panels, for example by one or more lines of attachment formed along the centerline of the absorbent composite, or along a line adjacent the crotch portions 16, 24 of the body panels, so as to allow the body panels to stretch from side to side and extend from front to back, or from the crotch to the waist.

Referring to FIGS. 1–8, the method for fabricating one or more embodiments of the aforedescribed refastenable absorbent garment is illustrated. Referring to FIGS. 1, 2, 6 and 7, a web 72 of body panel material is cut in a longitudinal machine direction 74 to form a front and rear body panel web 76, 78. Preferably, the web 72 is cut in a sinusoidal wave pattern, which should be broadly interpreted as a pattern having peaks 54, 154 and valleys 56, 156, with the pattern generally defined by a pitch P and an amplitude A, A1. The pattern can be formed of undulating curves or wave patterns, or can include or be made entirely of various linear portions.

Each body panel web includes an outer lateral edge 80, 82 and an inner cut edge 84, 86. In one embodiment, shown for example in FIG. 3, the inner cut edges 84, 86 of the front and rear body panel webs correspond, or mate such that they have the same shape and amplitude. In such an embodiment, no waste material is generated.

Figure 6:
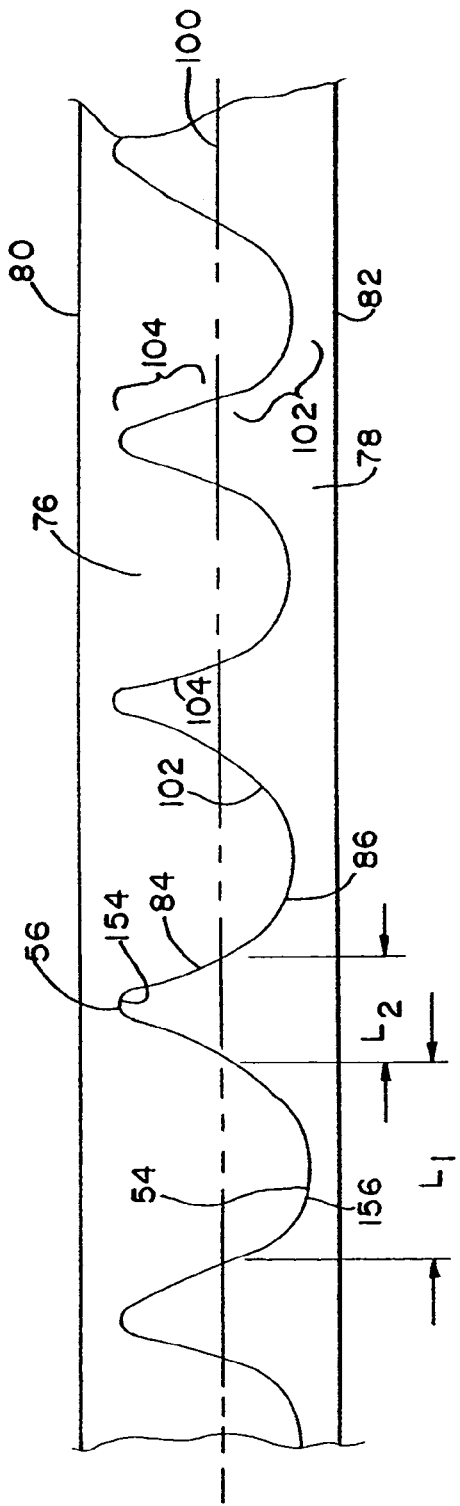
FIG. 6 is a plan view of a web of body panel material being cut along a longitudinal machine direction.
Figure 7:
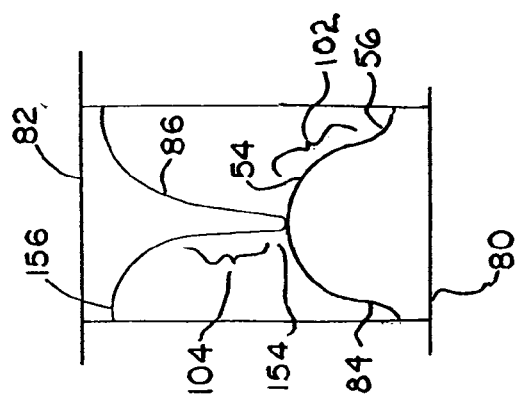
FIG. 7 is a plane view of a front and rear body panel web separated in the cross direction and aligned in the machine direction.
Figure 8:
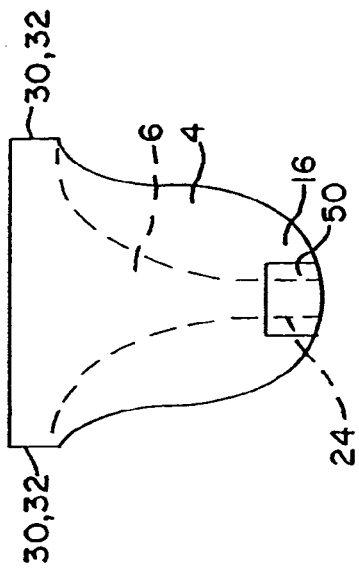
FIG. 8 is a garment having a front and rear body panel web formed from the webs shown in FIG. 7.

In an alternative preferred embodiment, shown in FIGS. 6–8, the wave pattern defining the first and second cut edges 84, 86 has a first and second shape 102, 104 formed on opposite sides of a wave baseline 100, which extends in the longitudinal machine direction approximately half way between the peaks 54, 154 and valleys 56, 156 of the cut edges. In this embodiment, the first shape 102 is different from said second shape 104, with each shape having a different curvature. In particular, the first shape 102 has a first wavelength L1 and the second shape 104 has a second wavelength L2. Preferably, the first wavelength L1 is greater than the second wavelength L2. In this way, as shown in FIG. 8, the front body panel 4 can be provided with a different shape than the rear body panel 6. For example, the undergarment can be configured as a thong shaped undergarment with a relatively narrow rear body panel 6.

In another preferred embodiment, a die cutter 100 is used to cut the web. The die cutter is configured to form inner cut edges 84, 86 on the front and rear body panels having different shapes and amplitudes A, A1, as shown for example in FIG. 2. In such an embodiment, a minimal amount of waste material is generated, but it allows for the front and rear body panels to be specifically shaped to conform to the body of the user. For example, the shape of the rear body panel web 78 cut edge 86 can be provided with lesser amplitude A1 than the amplitude A of the front body panel web 76. In this embodiment, a minimal amount of waste material 42 is produced. In one embodiment, one of the body panels is formed with a wave pattern, or substantially sinusoidal cut edge, while the other is configured with a straight cut edge. In various alternative embodiments, the cut edges can be formed by an oscillating cutter, slitters, water jets, lasers and other known cutting devices.

In the preferred embodiment, each of the front and rear body panel webs 76, 78 has a maximum rise (Max R), measured at the peak 54, 154, and a minimum rise (Min R), measured at the valley 56, 156. The term "rise," as used herein, means the measured distance between two edges, for example the outer edge 80, 82 and the inner cut edge 84, 86 of each of the front and rear body panel webs 76, 78 respectively. The total rise of the garment is measured between the outer edges 20, 28 of the front and rear body panels, or body panel webs, after the crotch member is connected thereto. Preferably, one or both of the front and rear body panel webs are shifted in the longitudinal machine direction, as shown to align the maximum rises, or peaks 54, 154, of the front and rear body panels, which also results in the alignment of the minimum rises, or valleys 56, 156, of the front and rear body panels. For example, as shown in FIG. 1, a first and second conveyor 102, 104 can simply be spaced apart so as to provide for a longer travel for one of the front and rear body panel webs 76, 78.

Referring to FIGS. 1 and 2, the front and rear body panel webs 76, 78 are also separated, or shifted, outwardly relative to one another in the lateral cross-direction 94 so as to form a gap 88 between the cut edges 84, 86 of the front and rear body panel webs 76, 78 at the maximum rise formed at the respective peaks 54, 154. In various embodiments, the spacing between the cut edges at the maximum rise of the respective front and rear body panels (i.e., the closest spacing between the front and rear body panels) is preferably between about 1% and about 90% of the total rise of the garment, more preferably between about 10% and about 60% of the total rise of the garment, and most preferably between about 20% and about 40% of the total rise of the garment. In addition, in various embodiments, the spacing between the cut edges at the maximum rise of the respective front and rear body panels is preferably between about 10 mm and about 800 mm, more preferably between about 50 mm and about 500 mm, and most preferably between about 100 mm and about 300 mm. In an alternative embodiment, the cut edges and the crotch portions of the front and rear body panels overlap, and can be secured one to the other. In such an embodiment, the panels can be separated slightly, or can simply be shifted in the longitudinal direction without any lateral separation.

In the preferred embodiment, the front and rear body panel webs 76, 78 are separated such that no portions of either web overlap each other. For example, and referring to FIG. 1, in one embodiment, a first pair of rollers 106 can be angled or twisted to laterally spread the front and rear body panel webs 76, 78 a first amount before they are shifted in the longitudinal machine direction. A second pair of rollers 108 can be angled or twisted to laterally spread the front and rear body panel webs 76, 78 a second amount after they are shifted in the longitudinal machine direction. Of course, it should be understood that the front and rear body panels can be first shifted in the longitudinal machine direction the desired amount and then separated in the lateral cross direction the entire desired amount, or they can also be first separated in the lateral cross direction the entire desired amount and then shifted in the longitudinal machine direction.

After the body panel webs 76, 78 are aligned and separated, regardless of the order thereof, a plurality of crotch members 50, for example absorbent inserts, are positioned in the lateral cross direction so as to bridge the gaps 88 between the body panel webs 76, 78 at successive peaks 54, 154 where the maximum rises of the body panel webs are aligned. It should be understood that the term "gap" as used herein includes a "zero" distance between the respective cut edges, wherein the cut edges abut but do not overlap. The crotch members 50 are secured to the body panel webs 76, 78 as explained above. It should be understood that the crotch members 50 are preferably secured to a bodyside surface 90, 92 of the body panel webs 76, 78, although they can also be secured to the garment side thereof. In a preferred embodiment, the crotch members, for example the absorbent inserts, are assembled offline and are then applied to the front and rear body panel webs 76, 78 as those webs are carried by a construction drum 110.

As shown in FIG. 1, the crotch member is preferably rotated using an offset cam action rotator 112. The rotator includes a plurality of transfer segments 126, which can have a vacuum applied thereto, that engage the crotch member 50. Coupler arms 127 connect the transfer segments and a drive ring. The coupler arm 127 includes a cam end having a cam follower that follows the profile of a cam mechanism. The profile of the cam mechanism can be readily changed to change the desired speed output and pitch of the crotch member. In one preferred embodiment, the rotator is configured to accelerate the crotch member. If the successive crotch members 50 are separated by a perforation, the transfer segment 126 breaks the perforation as it engages one crotch member and moves away from the next crotch member, which is engaged by a next transfer segment 126. The rotator rotates the end portion of the transfer segment, preferably approximately 90 degrees, about a radial axis, such that the crotch member is oriented in the machine direction as described above as the transfer segments are rotated about a horizontal axis 128. Alternatively, the landing material and fastener material are cut and separated by the transfer segments. The rotator, and the method for the use thereof, is further disclosed in U.S. Pat. Nos. 5,761,478, 5,759,340, and 6,139,004, and U.S. patent application Ser. No. 10/038,766, entitled "Apparatus For Applying Discrete Parts to A Moving Web," filed Jan. 2,2002, all of which are assigned to Kimberly-Clark Worldwide, Inc., the assignee of the present application, and the entire disclosures of all of which are hereby incorporated herein by reference. Alternatively, the subassembly can be rotated using a revolving transfer roll as shown and described in U.S. Pat. No. 4,608,115, which is assigned to Kimberly-Clark Worldwide, Inc., the assignee of the present application, and which is hereby incorporated herein by reference in its entirety.

Referring to FIGS. 1 and 4, after the crotch members 50 are secured to the body panel webs 76, 78 across the gap 88, the assembly is conveyed on a conveyor 114 to a helical folder 116, wherein the undergarments, and in particular the crotch members, are successively folded such that the front and rear body panel webs 76, 78 are positioned in an overlapping, or overlying relationship, preferably with the outer edges 80, 82 aligned. In various alternative embodiments, the body panel webs 76, 78 can be secured, for example by bonding, along a lateral cross direction at the area of minimum rise, or valleys 56, 156 to form the side seam 48. The front and rear body panel webs 76, 78 are then cut along the lateral cross direction along the seam 48 to form a plurality of discrete disposable undergarments, each having a front and rear body panel 4, 6. Alternatively, the front and rear body panel webs 76, 78 can be first cut at the area of minimum rise, or valleys 56, 156, and the crotch member 50 thereafter folded. Various refastenable fastening members can be applied to the front and rear body panels 4, 6 or front and rear body panel webs 76, 78 before or after the various cutting and folding operations. In yet another preferred embodiment, as explained above, the undergarment can be configured with side seams which secure the front and rear body panels, and refastenable fastening members, which bridge lines of weakness formed in one or the other of the body panels.

The elastic elements 36 are preferably incorporated into the web 72 of body panel material prior to cutting the web 72 to form the front and rear body panel webs 76, 78. If leg elastics are desired, preferably they are integrated into the web 72 along a pattern that will follow the cut edge 84, 86 on each of the front and rear body panel webs 76, 78. Of course, it should be understood that the elastics could be secured to the body panel webs after they are formed by the die cutter, or other cutting operation. In addition, the elastics can be non-continuous and intermittently spaced along the longitudinal direction such that they are incorporated along only the leg opening portions 18, 26 of the body panel webs and body panels.

The pitch (P) of the undergarment can be easily and quickly adjusted without the need to change over to new dies. The term "pitch" as used herein means the distance between any two adjacent things in series, and in particular between the valleys 56, 156 or side edges 30, 32 of the finished undergarment. In particular, the web 72 of body panel material is simply stretched or elongated various predetermined amounts before it is cut to form the front and rear body panel webs 76, 78. For example, the largest waist/hip size is provided when the web 72 of body panel material is introduced into the cutting operation, or die cutter, with no elongation or stretch in the longitudinal machine direction. The smallest waist/hip size is provided when the web 72 of body panel material is elongated or stretched to its maximum capability, such that after the cutting operation, the front and rear body panel webs 76, 78 retract to form a garment having a smaller pitch (P) between the valleys. In one preferred embodiment, the elongation of the body panel material is between about 20% and about 400%, in a more preferred embodiment the elongation is between about 50% and about 300%, and in a most preferred embodiment the elongation is between about 100% and about 200%. The final size or pitch of the undergarment is also determined by the process and positioning of the side seams, and the distance therebetween.

The rise (R) of the undergarment, measured between the outer edges 20, 28, also can be easily and quickly adjusted without the need to change over to new dies. In particular, the front and rear body panel webs are simply spaced apart in the lateral cross direction varying amounts, preferably with the gap being less than the length of the crotch member. For example, for a smaller garment having a lesser rise, the front and rear body panel webs 76, 78 are spaced closer together, with a smaller gap 88, than for a garment having a greater rise.

Preferably, the same crotch member 50 can be used in any of the garments, regardless of the pitch and rise. In this way, the overall simplicity and efficiency of the system and method is greatly improved, and there is no need to maintain inserts of different sizes in inventory, or to provide manufacturing capabilities to produce different size inserts. Indeed, the preferred embodiment of the method provides for a system of manufacturing a three-piece disposable undergarment with minimal waste, while providing flexibility to manufacture different size garments at minimal cost.

Although the present invention has been described with reference to preferred embodiments, those skilled in the art will recognize that changes may be made in form and detail without departing from the spirit and scope of the invention As such, it is intended that the foregoing detailed description be regarded as illustrative rather than limiting and that it is the appended claims, including all equivalents thereof, which are intended to define the scope of the invention.

What is claimed is:

1. A method of manufacturing a disposable undergarment comprising:
    moving a web of body panel material in a longitudinal machine direction;
    cutting said web of body panel material along said longitudinal machine direction and thereby forming a rear body panel web and a front body panel web each having a maximum rise and a minimum rise respectively, wherein said maximum rise of each of said rear and front body panel webs is greater than said minimum rise of a corresponding one of said rear and front body panel webs;
    shifting at least one of said rear and front body panel webs in said longitudinal machine direction and thereby aligning said maximum rises of said rear and front body panel webs;
    separating said rear and front body panel webs in a lateral cross direction, wherein said maximum rises of each of said rear and front body panel webs are spaced apart in said lateral cross direction and form a gap therebetween in a non-overlapping relationship;
    aligning a crotch member with each of said rear and front body panels at said maximum rises; and
    connecting said crotch member to each of said rear and front body panel webs and thereby bridging said gap therebetween.

2. The method of claim 1 wherein said cutting said web of body panel material along said longitudinal machine direction comprises forming a undulating wave pattern defining said maximum and minimum rises of each of said rear and front body panel webs.

3. The method of claim 2 wherein said wave pattern has a first and second shape formed on opposite sides of a wave baseline extending in the longitudinal machine direction, wherein said first shape is different from said second shape.

4. The method of claim 3 wherein said first shape has a first wavelength and wherein said second shape has a second wavelength, wherein said first wavelength is greater than said second wavelength.

5. The method of claim 1 further comprising cutting each of said front and rear body panel webs along said lateral cross direction proximate said minimum rise of each of said front and rear body panel webs after said connecting said crotch member to each of said rear and front body panel webs and thereby forming a plurality of discrete disposable undergarments each having a front body panel and a rear body panel respectively, wherein each of said front and rear body panels has opposite side edges.

6. The method of claim 5 further comprising folding said crotch member and thereby positioning one of said front and rear body panels in overlying relationship with the other thereof.

7. The method of claim 6 further comprising connecting said side edges of said front and rear body panels.

8. The method of claim 1 further comprising folding said crotch member and thereby positioning one of said front and rear body panel webs in overlying relationship with the other thereof.

9. The method of claim 8 further comprising cutting each of said front and rear body panel webs in said overlying relationship along said lateral cross direction proximate said minimum rise of each of said front and rear body panel webs and thereby forming a plurality of discrete disposable undergarments each having a front body panel and a rear body panel respectively.

10. The method of claim 8 further comprising connecting said overlying front and rear body panel webs at said minimum rise of each of said front and rear body panel webs.

11. The method of claim 1 further comprising elongating said web of body panel material in said longitudinal machine direction before said cutting said web of said body panel material.

12. The method of claim 1 wherein said cutting said web of body panel material along said longitudinal machine direction comprises forming a cut edge along each of said front and rear body panel webs, wherein said cut edges of said front and rear body panel webs have a first and second shape respectively, wherein said first shape is different than said second shape.

13. The method of claim 12 wherein said cutting said web of body panel material comprises die cutting said web of said body panel material.

14. The method of claim 1 wherein said separating said rear and front body panels in said lateral cross direction comprises varying the gap formed between said maximum rises of said rear and front body panel webs.

15. The method of claim 1 wherein said web of body panel material and each of said front and rear body panel webs have outer lateral edges and further comprising applying elastic elements in the longitudinal machine direction to at least one of said web of body panel material, said front body panel web and said rear body panel web adjacent said outer lateral edges thereof.

16. The method of claim 1 wherein said cutting said web of body panel material along said longitudinal machine direction comprises forming a pattern defining said maximum and minimum rises of each of said rear and front body panel webs and further comprising applying elastic elements in the longitudinal machine direction to at least one of said web of body panel material, said front body panel web and said rear body panel web adjacent at least one side of said pattern.

17. The method of claim 16 wherein said applying said elastic elements comprises applying said elastic elements to said web of body panel material adjacent both sides of said pattern before said cutting said web of body panel material.

18. The method of claim 1 wherein said front body panel web has a first amplitude substantially equal to the difference between said maximum and minimum rises of said front body panel web, and wherein said rear body panel web has a second amplitude substantially equal to the difference between said maximum and minimum rises of said rear body panel web, wherein said first amplitude is different than said second amplitude.

19. The method of claim 18 wherein said first amplitude is greater than said second amplitude.

20. The method of claim 1 wherein said crotch member comprises an absorbent insert.

21. The method of claim 1 wherein said gap is between about 10 mm and about 800 mm.

22. The method of claim 21 wherein said gap is between about 50 mm and about 500 mm.

23. The method of claim 22 wherein said gap is between about 100 mm and about 300 mm.

24. The method of claim 1 wherein said crotch member and said rear and front body panel webs define an overall rise of the disposable undergarment, and wherein said gap is between about 1% and about 90% of said overall rise.

25. The method of claim 24 wherein said gap is between about 10% and about 60% of said overall rise.

26. The method of claim 25 wherein said gap is between about 20% and about 40% of said overall rise.

27. A method of manufacturing a disposable undergarment comprising:
    moving a web of body panel material in a longitudinal machine direction;
    cutting said web of body panel material along said longitudinal machine direction in an undulating wave pattern and thereby forming a rear body panel web and a front body panel web each having an inner and outer edge respectively, wherein said inner edge of each of said front and rear body panel webs comprises alternating peaks and valleys defining crotch and leg opening portions respectively;
    shifting at least one of said rear and front body panel webs in said longitudinal machine direction and thereby aligning said crotch portions of said rear and front body panel webs;
    separating said rear and front body panel webs in a lateral cross direction, wherein said crotch portions of each of said rear and front body panel webs are spaced apart in said lateral cross direction and form a gap therebetween in a non-overlapping relationship; and
    bridging said gap between said crotch portions of said front and rear body panel webs with a crotch member.

28. The method of claim 27 further comprising cutting each of said front and rear body panel webs along said lateral cross direction at said leg opening portions thereof after said bridging said gap between said crotch portions of said front and rear body panel webs with said crotch member and thereby forming a plurality of discrete disposable undergarments each having a front body panel and a rear body panel respectively, wherein each of said front and rear body panels has opposite side edges.

29. The method of claim 27 further comprising folding said crotch member.

30. The method of claim 27 further comprising elongating said web of body panel material in said longitudinal machine direction before said cutting said web of said body panel material.

31. The method of claim 27 wherein said cutting said web of body panel material along said longitudinal machine direction comprises forming a cut edge along each of said front and rear body panel webs, wherein said cut edges of said front and rear body panel webs have a first and second shape respectively, wherein said first shape is different than said second shape.

32. The method of claim 31 wherein said cutting said web of body panel material comprises die cutting said web of said body panel material.

33. The method of claim 27 wherein said separating said rear and front body panels in a lateral cross direction comprises varying the gap formed between said maximum rises of said rear and front body panel webs.

34. The method of claim 27 wherein said web of body panel material and each of said front and rear body panel webs have outer lateral edges and further comprising securing elastic elements in the longitudinal machine direction to at least one of said web of body panel material, said front body panel web and said rear body panel web adjacent said outer lateral edges thereof.

35. The method of claim 27 wherein said cutting said web of body panel material along said longitudinal machine direction comprises forming a pattern defining said crotch and leg opening portions of each of said rear and front body panel webs and further comprising applying elastic elements in the longitudinal machine direction to said web of body panel material adjacent at least one side of said pattern before said cutting said web of body panel material.

36. The method of claim 27 wherein said crotch member is an absorbent insert.

37. The method of claim 27 wherein said wave pattern has a first and second shape formed on opposite sides of a wave baseline extending in the longitudinal machine direction, wherein said first shape is different from said second shape.

38. A method of manufacturing a disposable undergarment comprising:
    moving a web of body panel material in a longitudinal machine direction;
    elongating said web of body panel material in said longitudinal machine direction;
    cutting said web of body panel material along said longitudinal machine direction while said web of body panel material is elongated and thereby forming a rear body panel web and a front body panel web each having a maximum rise and a minimum rise respectively, wherein said maximum rise of each of said rear and front body panel webs is greater than said minimum rise of a corresponding one of said rear and front body panel webs;
    retracting said rear and front body panel webs in said longitudinal machine direction;
    shifting at least one of said rear and front body panel webs in said longitudinal machine direction and thereby aligning said maximum rises of said rear and front body panel webs; and
    connecting a crotch member to each of said rear and front body panel webs.

39. The method of claim 38 further comprising separating said rear and front body panel webs in a lateral cross direction, wherein said maximum rises of each of said rear and front body panel webs are spaced apart in said lateral cross direction and form a gap therebetween in a non-overlapping relationship, and aligning said crotch member with each of said rear and front body panels at said maximum rises.

40. The method of claim 39 wherein said separating said rear and front body panels in said lateral cross direction comprises varying the gap formed between said maximum rises of said rear and front body panel webs.

41. The method of claim 38 further comprising cutting each of said front and rear body panel webs along said lateral cross direction proximate said minimum rise of each of said front and rear body panel webs after said connecting said crotch member to each of said rear and front body panel webs and thereby forming a plurality of discrete disposable undergarments each having a front body panel and a rear body panel respectively.

\* \* \* \* \*